(12) United States Patent
Mizusawa (10) Patent No.: US 8,467,138 B2
(45) Date of Patent: Jun. 18, 2013

(54) OPTICAL ELEMENT AND OPTICAL UNIT USING THE SAME

(75) Inventor: Masayuki Mizusawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 143 days.

(21) Appl. No.: 13/138,201

(22) PCT Filed: Jan. 21, 2010

(86) PCT No.: PCT/JP2010/050713
§ 371 (c)(1),
(2), (4) Date: Jul. 18, 2011

(87) PCT Pub. No.: WO2010/084914
PCT Pub. Date: Jul. 29, 2010

(65) Prior Publication Data
US 2011/0279915 A1    Nov. 17, 2011

(30) Foreign Application Priority Data

Jan. 21, 2009  (JP) ................................. 2009-010695
Apr. 22, 2009  (JP) ................................. 2009-104027

(51) Int. Cl.
*G02B 7/02*    (2006.01)

(52) U.S. Cl.
USPC ........... 359/811; 359/365; 359/680; 359/725; 359/726; 359/727; 359/736

(58) Field of Classification Search
USPC ................. 359/811, 819, 642, 682, 364–366, 359/680, 689, 725–727, 736, 738, 740, 871, 359/850; 348/36, 38, 39
See application file for complete search history.

(56) References Cited

U.S. PATENT DOCUMENTS

| | | | | |
|---|---|---|---|---|
| 7,408,703 | B2 * | 8/2008 | Matsuki et al. | 359/365 |
| 7,463,431 | B2 * | 12/2008 | Togino et al. | 359/725 |
| 7,929,219 | B2 * | 4/2011 | Togino | 359/736 |
| 8,254,038 | B2 * | 8/2012 | Togino | 359/725 |
| 8,284,494 | B2 * | 10/2012 | Mizusawa | 359/680 |
| 8,310,769 | B2 * | 11/2012 | Mizusawa | 359/736 |
| 2011/0273784 | A1 * | 11/2011 | Mizusawa | 359/727 |

FOREIGN PATENT DOCUMENTS

| | | |
|---|---|---|
| JP | 7-318799 | 12/1995 |
| JP | 2001-267594 | 9/2001 |
| JP | 2002-233494 | 8/2002 |

(Continued)

OTHER PUBLICATIONS

International Search Report dated Apr. 20 2010, issued in corresponding International Application No. PCT/JP2010/050713.

*Primary Examiner* — Loha Ben
(74) *Attorney, Agent, or Firm* — Kenyon & Kenyon LLP (57) ABSTRACT

An optical element of the present invention is provide with a first surface which is formed on the front-object side and upon which light from the front-object side is incident, a second surface formed on the image side, and a third surface which is formed between the first surface and the second surface and upon which light from the generally lateral object side is incident. The first surface is provided with a first transmission surface formed around the optical axis and a first reflection surface which faces the image side and which is formed annularly around the first transmission surface. The second surface is provided with a second transmission surface formed around the optical axis, and a second reflection surface which faces the front object side and which is formed annularly around the second transmission surface.

15 Claims, 6 Drawing Sheets

FOREIGN PATENT DOCUMENTS

| WO | 03/042743 | 5/2003 |
| WO | 2005/110186 | 11/2005 |
| WO | WO 2007/108257 | 9/2007 |
| WO | WO 2008/153114 | 12/2008 |

* cited by examiner

OPTICAL ELEMENT AND OPTICAL UNIT USING THE SAME

This application is a 371 of PCT/JP2010/050713 dated Jan. 21, 2010.

TECHNICAL FIELD

This invention relates to an optical element by which a front object and an approximately lateral object can be simultaneously observed and to an optical unit using the optical element.

BACKGROUND ART

Optical units which are provided with an optical system by which a front object and an approximately lateral object can be simultaneously observed and a lens barrel that holds the optical system have been known up to now. In this case, the range which the above term, "approximately lateral", defines includes not only the lateral side of the optical system itself but also the diagonally forward and diagonally backward sides of the optical system.

In optical systems for such optical units, an optical system which is formed in such a way that, after light from the approximately-lateral-object side is reflected two times on the inside, the light emerges to the image side to be guided to an imaging element like CCD (Charge Coupled Device), CMOS (Complementary Metal-Oxide Semiconductor), or the like has been known (for example, refer to International Publication No. 2003/042743).

DISCLOSURE OF INVENTION

However, in the optical system which is described in International Publication No. 2003/042743, after light from the approximately-lateral-object side is reflected by two members, the light emerges to the image side. Accordingly, the optical system which is described in International Publication No. 2003/042743 has a problem that, in the case where cumulative tolerance between these members and the lens barrel that holds these members becomes large, one of these members easily becomes eccentric to the other of these members in assembling the optical unit and the capability of forming an image easily deteriorates.

The present invention is made in view of such a conventional technical problem. The object of the present invention is to offer an optical element and an optical unit which can restrain the deterioration of the capability of forming an image.

In order to achieve the above-described object, an optical element of the present invention is characterized in that the optical element is provided with a first surface which is formed on the front-object side and through which light from the front-object side enters, a second surface which is formed on the image side, and a third surface which is formed between the first and second surfaces and through which light from the approximately-lateral-object side enters, wherein the first surface is provided with a first transmission surface which is formed with the center of the first transmission surface being on the optical axis and a first reflection surface which faces toward the image side and is formed around the first transmission surface and in the shape of a ring, and the second surface is provided with a second transmission surface which is formed with the center of the second transmission surface being on the optical axis and a second reflection surface which faces toward the front-object side and is formed around the second transmission surface and in the shape of a ring.

Also, in an optical element of the present invention, it is preferred that: after light from the front-object side is incident on the first transmission surface, the light emerges from the second transmission surface to the image side; and after light from the approximately-lateral-object side is incident on the third surface, the light is reflected by the second reflection surface and the first reflection surface in that order and emerges from the second transmission surface to the image side.

Also, in order to achieve the above-described object, an optical unit of the present invention is characterized in that the optical unit is provided with an optical system by which a front object and an approximately lateral object are observed, and a lens barrel which holds the optical system, wherein the optical system includes one of the above-described optical elements, the lens barrel at least has a first lens barrel and a second lens barrel, the first lens barrel is fitted to the first surface of the optical element, and the second lens barrel is fitted to the second surface of the optical element.

Also, in an optical unit of the present invention, it is preferred that the external peripheral surface of the optical unit is composed of the external peripheral surface of the lens barrel and the third surface.

Also, in an optical unit of the present invention, it is preferred that the optical system comprises a first optical system and a second optical system, the first optical system is provided with a first lens group having negative refractive power, a second lens group including the optical element, and a third lens group in order from the front-object side, and the second optical system is provided with the second lens group and the third lens group in order from the approximately-lateral-object side.

Also, in an optical unit of the present invention, it is preferred that a first fitting portion is formed around the first reflection surface of the optical element, a second fitting portion is formed around the second reflection surface of the optical element, the first lens barrel is fitted to the first fitting portion, and the second lens barrel is fitted to the second fitting portion.

Also, in an optical unit of the present invention, it is preferred that at least one of the first and second fitting portions is formed in the shape of a step.

Also, in an optical unit of the present invention, it is preferred that the first and second fitting portions are formed in such a way that the first and second fitting portions are rotationally symmetric relative to the optical axis.

Also, in an optical unit of the present invention, it is preferred that the first lens barrel includes a first holding portion, the second lens barrel includes a second holding portion, the first holding portion holds the optical element through the first surface of the optical element, the second holding portion holds the optical element through the second surface of the optical element, and at least one of the first and second holding portions is formed in the shape of a step.

Also, in an optical unit of the present invention, it is preferred that the first and second holding portions are formed in such a way that the first and second holding portions are rotationally symmetric relative to the optical axis.

Also, in order to achieve the above-described object, an optical unit of the present invention is characterized in that the optical unit comprises an optical system by which a front object and an approximately lateral object are observed, a lens barrel which holds the optical system, and an imaging element, wherein the optical system includes a lens group which includes the optical element and a lens group which is arranged nearer to the image side than the lens group including the optical element and includes an aperture stop, and the optical unit is provided with an annular light-shielding member which is placed in the vicinity of the aperture stop, is made of light-shielding material, and has an internal diameter that is larger than the internal diameter of the aperture stop and smaller than the internal diameter of the lens barrel.

Also, in an optical unit of the present invention, it is preferred that the aperture stop is formed integratedly with the light-shielding member.

Also, in an optical unit of the present invention, it is preferred that the imaging element is held by the lens barrel.

Also, in an optical unit of the present invention, it is preferred that the lens barrel consists of: an internal barrel which holds a lens group that is arranged nearer to the image side than the optical element; and an external barrel which holds the internal barrel, and the light-shielding member is formed integratedly with the internal barrel.

Also, in an optical unit of the present invention, it is preferred that the external diameter of the light-shielding member approximately corresponds with the internal diameter of the lens barrel.

According to the present invention, it is possible to offer an optical element and an optical unit which can restrain the deterioration of the capability of forming an image.

BEST CONFIGURATION FOR EMBODYING INVENTION

The embodiments of the present invention will be explained in detail below.

Embodiment 1

Figure 1:
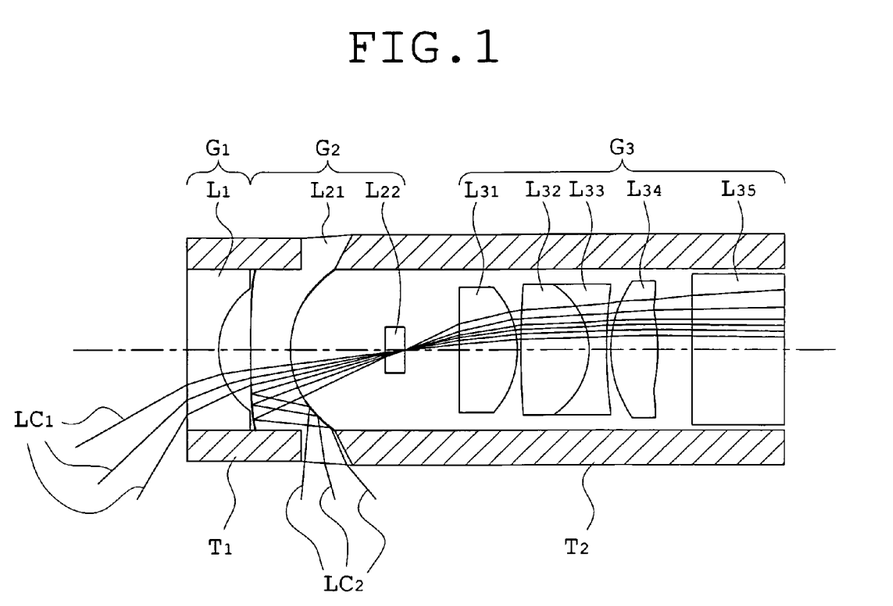
FIG. 1 is a schematic view showing the optical unit according to an embodiment 1 of the present invention.

First, the constitution of the optical unit of the present embodiment is explained using FIG. 1. The optical unit of the present embodiment comprises: an optical system which consists of three lens groups and by which a front object and an approximately lateral object can be simultaneously observed; and two lens barrels which hold the optical system. Besides, an imaging element like CCD, CMOS, or the like is arranged at the rear of the optical system (on the image side), although the imaging element is not shown in the drawings in the present embodiment. Also, low pass filter which is given IR cut coating, CCD-cover glass, or the like may be arranged between the optical system and the imaging element.

The optical system of the present embodiment by which a front object and an approximately lateral object can be simultaneously observed includes, in order from the front-object side, a first lens group $G_1$ through which light from the front-object side enters, a second lens group $G_2$ through which light transmitted by the lens group $G_1$ and light from the approximately-lateral-object side enter, and a third lens group $G_3$. In this case, the first lens group $G_1$ has negative refractive power. Also, the third lens group $G_3$ has positive refractive power.

The first lens group $G_1$ is composed of a lens $L_1$ which is a plano-concave lens the concave surface of which faces toward the image side. The second lens group $G_2$ is composed of: a lens $L_{21}$ which is an optical element for simultaneously observing a front object and an approximately lateral object and has a special shape; and a plano lens $L_{22}$ to which an aperture stop is integratedly fitted on the image side, in that order from the front-object side. The third lens group $G_3$ is composed of: a plano-convex lens $L_{31}$ the convex surface of which faces toward the image side; a cemented lens which consists of a biconvex lens $L_{32}$ and a biconcave lens $L_{33}$; a biconvex lens $L_{34}$ the image-side surface of which is an aspherical surface; and a plano lens $L_{35}$, in that order from the front-object side. Besides, the shapes of the lenses except the lens $L_{21}$ are not limited to the above-described shapes.

Figure 2:
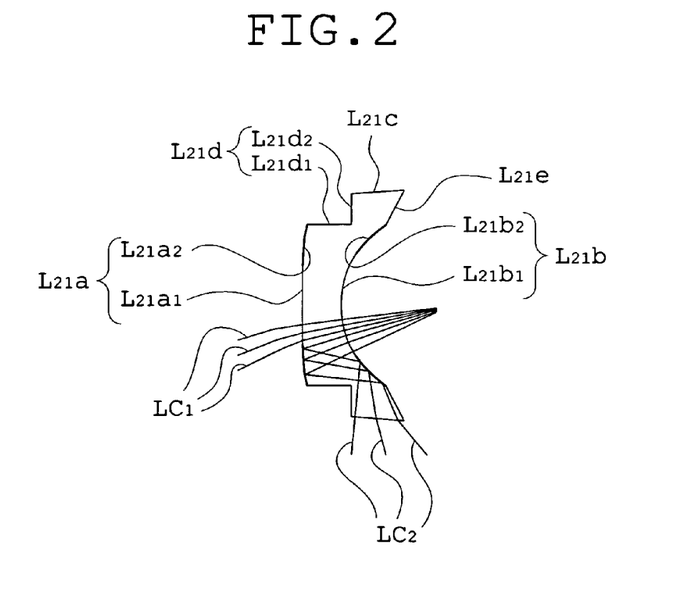
FIG. 2 is a schematic view showing an optical element which included by an optical system that is provided for the optical unit that is shown in FIG. 1.

Now, the lens $L_{21}$ which is an optical element for simultaneously observing a front object and an approximately lateral object and has a special shape is explained in detail using FIG. 2. The lens $L_{21}$ has: a first surface $L_{21}a$ which is formed on the front-object side and through which light from the front-object side enters; a second surface $L_{21}b$ which is formed on the image side; and a third surface $L_{21}c$ which is formed in the circumferential direction so as to surround the optical axis between the first surface $L_{21}a$ and the second surface $L_{21}b$ and through which light from the approximately-lateral-object side enters. This third surface $L_{21}c$ may be formed on a part of or on the whole of the surface in the circumferential direction between the first surface $L_{21}a$ and the second surface $L_{21}b$. Also, a first fitting portion $L_{21}d$ is formed between the first surface $L_{21}a$ and the third surface $L_{21}c$ and a second fitting portion $L_{21}e$ is formed between the second surface $L_{21}b$ and the third surface $L_{21}c$.

The first surface $L_{21}a$ of the lens $L_{21}$ includes: a first transmission surface $L_{21}a_1$ which is formed with the center of the first transmission surface $L_{21}a_1$ being on the optical axis; and a first reflection surface $L_{21}a_2$ which faces toward the image side and is formed around the first transmission surface $L_{21}a_1$ and in the shape of a ring. The second surface $L_{21}b$ includes:

a second transmission surface $L_{21}b_1$ which is formed with the center of the second transmission surface $L_{21}b_1$ being on the optical axis; and a second reflection surface $L_{21}b_2$ which faces toward the front-object side and is formed around the second transmission surface $L_{21}b_1$ and in the shape of a ring. Besides, in the present embodiment, the third surface $L_{21}c$ is formed in such a way that the image-side diameter of the third surface $L_{21}c$ is larger than the front-object-side diameter of the third surface $L_{21}c$. However, the third surface $L_{21}c$ may be formed in such a way that the image-side diameter of the third surface $L_{21}c$ is smaller than the front-object-side diameter of the third surface $L_{21}c$. In this case, the above word, "the front-object-side diameter", means "the diameter in the surface which is located at the position nearest to the front-object side in the third surface $L_{21}c$ and is perpendicular to the optical axis". Also, the above word, "the image-side diameter", means "the diameter in the surface which is located at the position nearest to the image side in the third surface $L_{21}c$ and is perpendicular to the optical axis".

Besides, the first reflection surface $L_{21}a_2$ and the second reflection surface $L_{21}b_2$ are formed through vapor deposition. Specifically, for example, after a mask which has the same shape as that of the first transmission surface $L_{21}a_1$ is put on the first transmission surface $L_{21}a_1$, the whole of the first surface $L_{21}a$ is given mirror coating, and then, the mask is peeled off from the first transmission surface $L_{21}a_1$. A masked part of the first surface $L_{21}a$ is not given mirror coating by the use of such a method, so that the first transmission surface $L_{21}a_1$ can be used as a transmission surface even after the first reflection surface $L_{21}a_2$ is formed. Besides, methods for forming the first reflection surface $L_{21}a_2$ and the second reflection surface $L_{21}b_2$ are not limited to the above-described manner.

Also, a first fitting portion $L_{21}d$ is formed around the first reflection surface $L_{21}a_2$ of the first surface $L_{21}a$ of the lens $L_{21}$. The first fitting portion $L_{21}d$ is fitted to a first lens barrel $T_1$, as shown in FIG. 1. Besides, the first fitting portion $L_{21}d$ is formed by a cylindrical surface $L_{21}d_1$ the center of which is on the optical axis and an annular surface $L_{21}d_2$ which is approximately perpendicular to the optical axis, in such a way that the first fitting portion $L_{21}d$ is formed annularly and in the shape of a step. On the other hand, a second fitting portion $L_{21}e$ to which a second lens barrel $T_2$ holding the second lens group $G_2$ is fitted as shown in FIG. 1 is formed around the second reflection surface $L_{21}b_2$ of the second surface $L_{21}d$ of the lens $L_{21}$. As described above, the fitting portion for fitting the lens barrel is provided for the lens $L_{21}$ which is an optical system for simultaneously observing a front object and an approximately lateral object in the optical unit of the present embodiment, so that there is no necessity for providing an optical unit with a holding member that is larger than the diameters of lenses of its optical system as in conventional optical units. In this case, the first lens barrel $T_1$, the lens $L_{21}$, and the second lens barrel $T_2$ are arranged in such a way that each of the first lens barrel $T_1$, the lens $L_{21}$, and the second lens barrel $T_2$ is rotationally symmetric relative to the optical axis. In addition, the first fitting portion $L_{21}d$ is also formed in such a way that the first fitting portion $L_{21}d$ is rotationally symmetric relative to the optical axis.

Next, paths which light rays having entered the optical system of the optical unit of the present embodiment follow are explained using FIGS. 1 and 2. Light rays $LC_1$ which enters the optical system of the optical unit of the present embodiment from the front-object side first pass through a lens $L_1$. And, the light rays $LC_1$ which have passed through the lens $L_1$ enter the first transmission surface $L_{21}a_1$ of the first surface $L_{21}a$ of the lens $L_{21}$. Thereafter, the light rays $LC_1$ which have entered the first transmission surface $L_{21}a_1$ emerge from the second transmission surface $L_{21}b_1$ of the second surface $L_{21}b$ of the lens $L_{21}$. The light rays $LC_1$ which have emerged from the second transmission surface $L_{21}b_1$ pass through a lens $L_{22}$, a lens $L_{31}$, a lens $L_{32}$, a lens $L_{33}$, a lens $L_{34}$, and a lens $L_{35}$, in that order, and then the light rays $LC_1$ enter an imaging element. As a result, the image of the front object is formed on the imaging element.

On the other hand, light rays $LC_2$ which enters the optical system of the optical unit of the present embodiment from the approximately-lateral-object side first enters the third surface $L_{21}c$ of the lens $L_{21}$. And, the light rays $LC_2$ which have entered the third surface $L_{21}c$ are reflected to the object side by the second reflection surface $L_{21}b_2$ of the second surface $L_{21}b$ of the lens $L_{21}$. Thereafter, the light rays $LC_2$ which have reflected by the second reflection surface $L_{21}b_2$ are reflected to the image side by the first reflection surface $L_{21}a_2$ of the first surface $L_{21}a$ of the lens $L_{21}$. Further thereafter, the light rays $LC_2$ which have reflected by the first reflection surface $L_{21}a_2$ emerge from the second transmission surface $L_{21}b_1$ of the second surface $L_{21}b$ of the lens $L_{21}$. The light rays $LC_2$ which have emerged from the second transmission surface $L_{21}b_1$ pass through the lens $L_{22}$, the lens $L_{31}$, the lens $L_{32}$, the lens $L_{33}$, the lens $L_{34}$, and the lens $L_{35}$, in that order, and then the light rays $LC_2$ enter the imaging element. As a result, the image of the approximately lateral object is formed on the imaging element.

The lens group $G_2$ of the optical system that constitutes the optical unit of the present embodiment includes the lens $L_{21}$. And, this lens $L_{21}$ is an optical element having the first reflection surface $L_{21}a_2$ and the second reflection surface $L_{21}b_2$. Accordingly, as a result of making the lens $L_{21}$ with sufficient precision, the relation between the two reflection surfaces arranged also has sufficient precision, so that it is possible to prevent the first reflection surface $L_{21}a_2$ from becoming eccentric to the second reflection surface $L_{21}b_2$ in assembling the optical unit. As a result, in optical units for which optical elements like the lens $L_{21}$ in the present embodiment are used, it is hard for one member (the first reflection surface $L_{21}a_2$) to become eccentric to the other member (the second reflection surface $L_{21}b_2$) as in the prior art, and it is possible to prevent the deterioration of a capability of forming an image.

Also, every one of the first lens barrel $T_1$, the lens $L_{21}$, and the second lens barrel $T_2$ is arranged in such a way that the every one is rotationally symmetric to the optical axis. As a result, the optical axes of the first lens group $G_1$ held by the first lens barrel $T_1$, the second lens group $G_2$ including the lens $L_{21}$, and the second lens group $G_2$ held by the second lens barrel $T_2$ can be easily made to correspond with one another in assembling the optical unit. Accordingly, it is possible to prevent a plurality of the lenses from becoming eccentric to one another, and it is possible to prevent the deterioration of the capability of forming an image.

Also, the first fitting portion $L_{21}d$ is also formed in such a way that the first fitting portion $L_{21}d$ is rotationally symmetric to the optical axis. Accordingly, an adjustment of eccentricity is easily made while the first lens barrel $T_1$ and the lens $L_{21}$ are being rotated about the optical axis in assembling the optical unit. Accordingly, in the optical unit of the present embodiment, it is hard for the first lens barrel $T_1$ and the lens $L_{21}$ to become eccentric to each other, and it is possible to prevent the deterioration of the capability of forming an image due to eccentricity.

Besides, in the above-described embodiment, two lens barrels are fitted to fitting portions which are formed in an optical element, respectively. However, the two lens barrels $T_1$ and $T_2$ may be fitted directly to the non-reflection surfaces on the back sides of the two reflection surfaces of the lens $L_{21}$ that is the optical element, respectively, without forming the fitting portions in the optical element.

Figure 3:
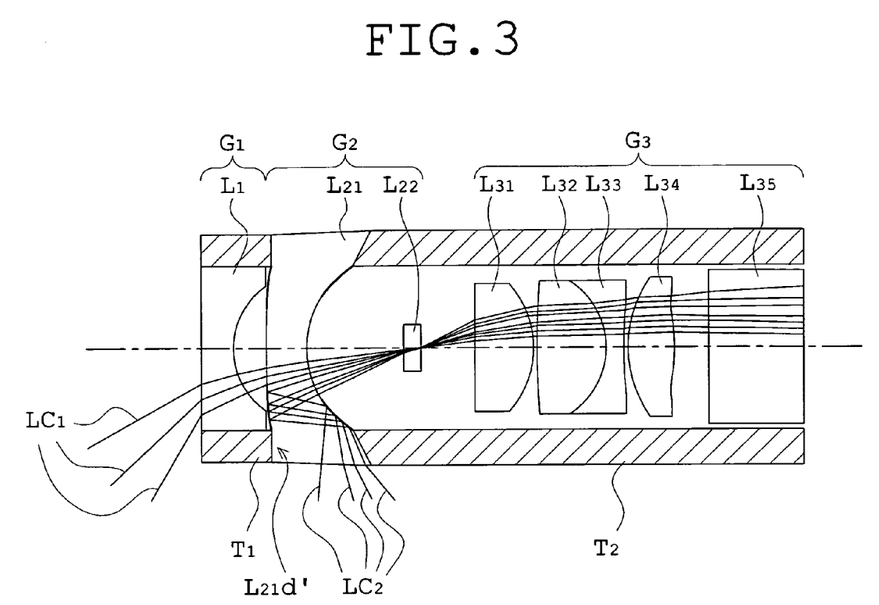
FIG. 3 is a schematic view showing a variation of the optical unit according to the embodiment 1 of the present invention.

Also, in the above-described embodiment, the first fitting portion $L_{21}d$ is formed in the shape of a step. However, there is not necessity to necessarily form the first fitting portion $L_{21}d$ in such a shape. For example, like a first fitting portion $L_{21}d'$ in a variation of the optical unit according to the present invention which is shown in FIG. 3, a first fitting portion may be formed in such a way that the object-side surface of the first fitting portion has no difference in level from the first surface $L_{21}a$.

Figure 4:
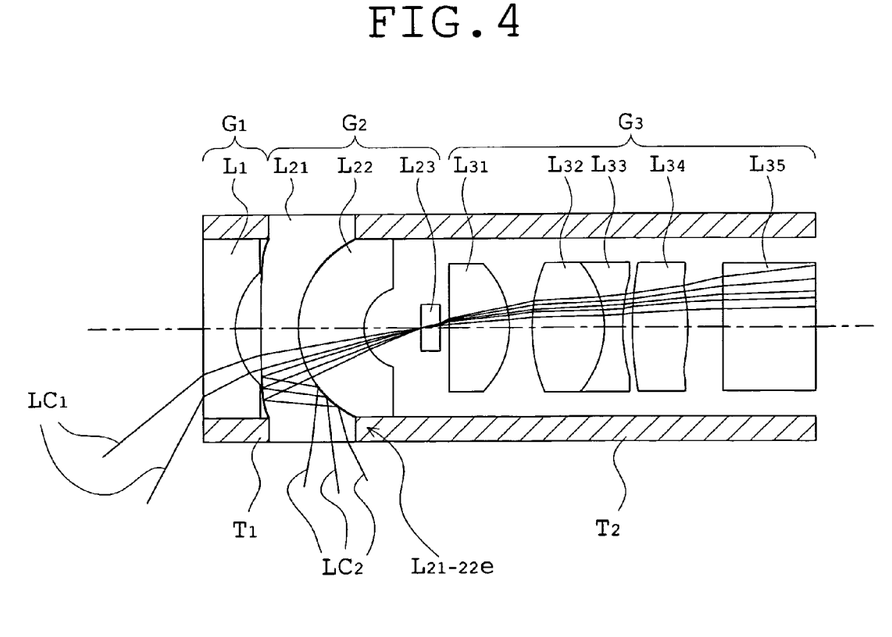
FIG. 4 is a schematic view showing a variation of the optical unit according to the embodiment 1 of the present invention.

Also, in the above-described embodiment, the step-shaped first fitting portion $L_{21}d$ is formed on the front-object side of the optical element. However, there is not necessity to necessarily form such a fitting portion on the front-object side of the optical element. As in a variation of the optical unit according to the present invention which is shown in FIG. 4, an optical element may be composed of the lens $L_{21}$ and the lens $L_{22}$ which are included by the second lens group $G_2$, so that a step-shaped second fitting portion $L_{21-22}e$ is formed on the image side of the optical element.

Besides, in this variation, the second fitting portion $L_{21-22}e$ is formed in such a way that the second fitting portion $L_{21-22}e$ is rotationally symmetric to the optical axis. As a result, the second lens barrel $T_2$ and the optical element can be easily touched to each other to be assembled. Accordingly, in the optical unit of the present variation, it is hard for both of them to become eccentric, and it is possible to prevent the deterioration of the capability of forming an image due to eccentricity.

Also, in this variation, the step-shaped second fitting portion $L_{21-22}e$ is formed on the image side of the optical element by making the optical element of two lenses. However, by the use of the same method as the above-described method of forming the first fitting portion $L_{21}d$ in the embodiment, a step-shaped second fitting portion may be formed in one lens, for example, only in the lens $L_{21}$.

Figure 5:
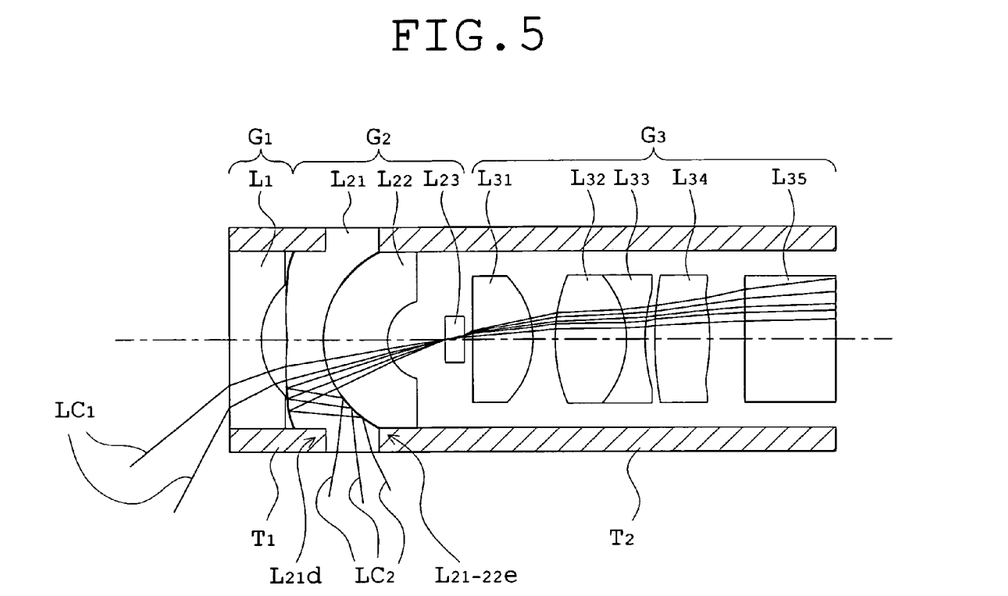
FIG. 5 is a schematic view showing a variation of the optical unit according to the embodiment 1 of the present invention.

Also, in the above-described embodiment and variation, the step-shaped fitting portion is formed only on either of the object side or the image side of the optical element. However, like the first fitting portion $L_{21}d$ and the second fitting portion $L_{21-22}e$ in a variation of the optical unit according to the present invention which is shown in FIG. 5, fitting portions may be formed in the both surfaces of the optical element.

Besides, in this variation, every one of the first fitting portion $L_{21}d$ and the second fitting portion $L_{21-22}e$ is formed in such a way that the every one is rotationally symmetric to the optical axis. As a result, the first lens barrel $T_1$ and the second lens barrel $T_2$ can be easily touched to the first fitting portion $L_{21}d$ and the second fitting portion $L_{21-22}e$ of the optical element respectively to be assembled. Accordingly, in the optical unit of the present variation, it is hard for the optical element, the first lens barrel $T_1$, and the second lens barrel $T_2$ to become eccentric, and it is possible to prevent the deterioration of the capability of forming an image due to eccentricity.

Figure 6:
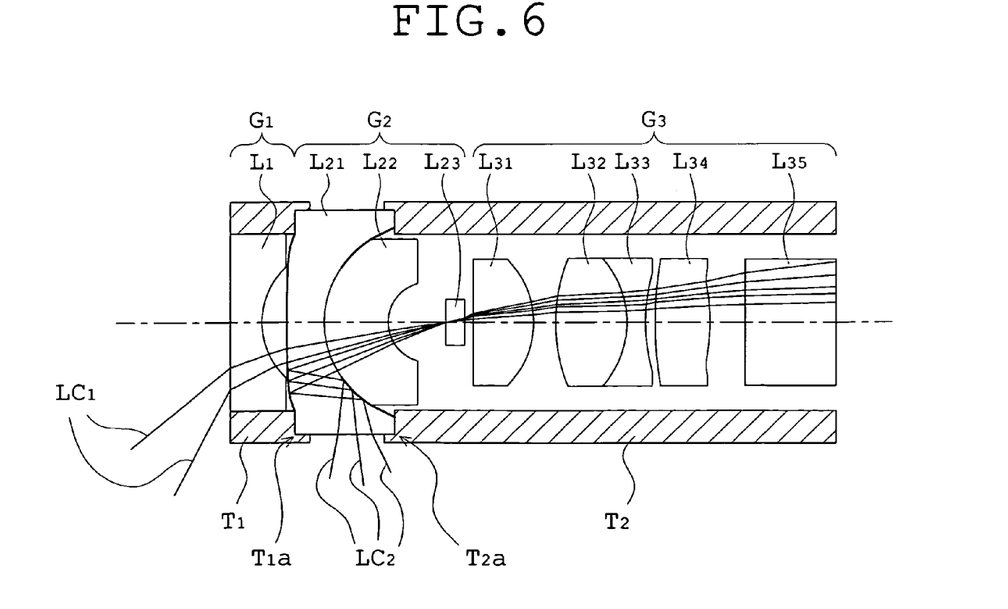
FIG. 6 is a schematic view showing a variation of the optical unit according to the embodiment 1 of the present invention.

Also, in the above-described embodiment and variation, the fitting portion is formed in the optical element. However, instead of forming the fitting portion in the optical element, a holding portion may be formed in one of or both of a surface of the first lens barrel which is fitted to the first surface of the optical element and a surface of the second lens barrel which is fitted to the second surface of the optical element. For example, as in a variation of the optical unit according to the present invention which is shown in FIG. 6, a first holding portion $T_1a$ may be formed on the edge of the first lens barrel $T_1$ on the lens-$L_{21}$ side, and a second holding portion $T_2a$ may be formed on the edge of the second lens barrel $T_2$ on the front-object side.

Besides, in this variation, the first holding portion $T_1a$ and the second holding portion $T_2a$ are formed in the shape of a step and in such a way that the first holding portion $T_1a$ and the second holding portion $T_2a$ are rotationally symmetric to the optical axis. As a result, the first holding portion $T_1a$ and the second holding portion $T_2a$ can be easily touched to the optical element to be assembled. Accordingly, in the optical unit of the present variation, it is hard for the optical element, the first lens barrel $T_1$, and the second lens barrel $T_2$ to become eccentric, and it is possible to prevent the deterioration of the capability of forming an image due to eccentricity.

Embodiment 2

Figure 7:
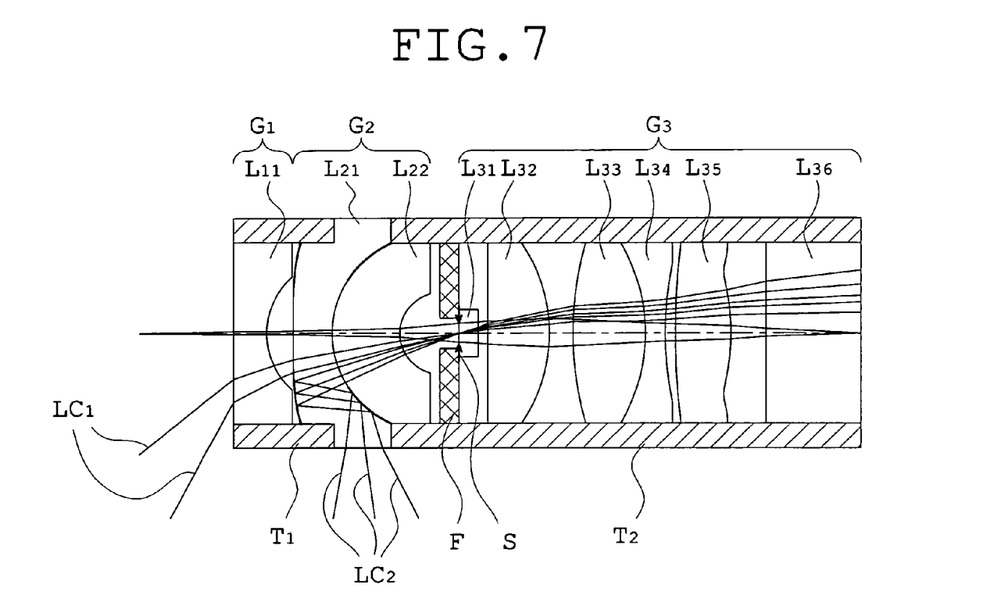
FIG. 7 is a schematic view showing the optical unit according to an embodiment 2 of the present invention.

Next, the optical unit according to the embodiment 2 will be explained in detail using FIG. 7. Besides, because the optical system which constitutes the optical unit of the present embodiment has approximately the same constitution as that of the optical system of the above-described embodiment 1, the explanations of the lens $L_{21}$ that is the optical element and the paths which light rays having entered this optical system follow are omitted.

This optical unit comprises an optical system which consists of three lens groups, an annular light-shielding member which is inserted into the optical system, an imaging element having an image plane on which an image is formed by the optical system, and a lens barrel which holds the optical system, the light-shielding member, and the imaging element. Besides, an imaging element like CCD, CMOS, or the like is arranged at the rear of the optical system (on the image side), although the imaging element is not shown in the drawings in the present embodiment. Also, low pass filter which is given IR cut coating, CCD-cover glass, or the like may be arranged between the optical system and the imaging element.

The optical system in the present embodiment by which a front object and an approximately lateral object can be simultaneously observed includes, in order from the front-object side, a first lens group $G_1$ which has negative refractive power, a second lens group $G_2$, and a third lens group $G_3$ which has positive refractive power. Besides, the third lens group $G_3$ is provided with an aperture stop S.

And, in light entering the optical system, light from the front-object side enters the first lens group $G_1$, the second lens group $G_2$, and the third lens group $G_3$, in that order. On the other hand, light from the approximately-lateral-object side enters the second lens group $G_2$ and the third lens group $G_3$, in that order.

Also, this optical system is formed in such a way that the optical system is a retro-focus type optical system for both light from the front-object side and light from the approximately-lateral-object side. The use of such a constitution of the optical system can make an angle of view for observation large.

The first lens group $G_1$ is composed of a lens $L_{11}$ which is a plano-concave lens the concave surface of which faces toward the image side. The second lens group $G_2$ is composed of a cemented lens which consists of: a lens $L_{21}$ that is an optical element for simultaneously observing a front object and an approximately lateral object and has a special shape; and a lens $L_{22}$ that is a negative meniscus lens the convex surface of which faces toward the front-object side, in that order from the front-object side. The third lens group $G_3$ is composed of: a lens $L_{31}$ which is a plano lens; a lens $L_{32}$ which is a plano-convex lens the convex surface of which faces toward the image side; a lens $L_{33}$ which is a biconvex lens; a lens $L_{34}$ which is a biconcave lens; a lens $L_{35}$ which is a biconvex lens the image-side surface of which is an aspherical surface; and a lens $L_{36}$ which is a plano lens, in that order from the front-object side. Besides, an aperture stop S is provided on the front-object side of the lens $L_{31}$ and integratedly with the lens $L_{31}$. Also, the lens $L_{33}$ and the lens $L_{34}$ that is a biconcave lens are jointed together to constitute a cemented lens.

Also, the lens barrel which holds the optical system, the light-shielding member, and the imaging element is composed of a first lens barrel $T_1$ and a second lens barrel $T_2$.

The first lens barrel $T_1$ holds the first lens group $G_1$ and the second lens group $G_2$. More specifically, the first lens barrel $T_1$ holds the first lens group $G_1$ on the inside of first lens barrel $T_1$. Also, the first fitting portion $L_{21}d$ of the lens $L_{21}$ that is the optical element is fitted to the first lens barrel $T_1$ on the image side of the first lens barrel $T_1$, so that the first lens barrel $T_1$ holds the lens $L_{21}$. That is to say, a part of the internal peripheral surface of the first lens barrel $T_1$ comes into contact with the peripheral surface of the lens $L_{11}$. Also, a part of the internal peripheral surface of the first lens barrel $T_1$ and the image-side plane of the first lens barrel $T_1$ come into contact with the first fitting portion $L_{21}d$.

On the other hand, the second lens barrel $T_2$ holds the second lens group $G_2$, the light-shielding member F, the third lens group $G_3$, and the imaging element. More specifically, the second fitting portion $L_{21}e$ of the lens $L_{21}$ that is the optical member is fitted to the front object-side edge plane of the second lens barrel $T_2$, so that the second lens barrel $T_2$ holds the lens $L_{21}$. Also, the second lens barrel $T_2$ holds the lens $L_{22}$ on the inside of the second lens barrel $T_2$. That is to say, a part of the internal peripheral surface of the second lens barrel $T_2$ comes into contact with the peripheral surface of the lens $L_{22}$. Also, the front object-side plane of the second lens barrel $T_2$ comes into contact with the second fitting portion $L_{21}e$.

As described above, a fitting portion which is fitted to the lens barrel is provided for the lens $L_{21}$ that is the optical element in the optical unit of the present embodiment, so that the lens $L_{21}$ that is the optical element can be fitted directly to the lens barrel. As a result, there is no necessity for providing the optical unit of the present embodiment with a holding portion which is larger than the diameters of lenses of the optical system as in prior optical units, and it is possible to downsize the whole of the apparatus, as compared with prior optical units.

Besides, the first and second lens barrels $T_1$ and $T_2$ are formed in such a way that the external peripheral surfaces of the first and second lens barrels $T_1$ and $T_2$ approximately correspond with the external peripheral surface of the third surface of the lens $L_{21}$. And, these surfaces form the external peripheral surface of the optical unit.

Also, the annular light-shielding member F which is inserted into the optical system is arranged nearer to the object side than the aperture stop S. Also, the light-shielding member F is formed in such a way that the internal diameter of the light-shielding member F is larger than that of the aperture stop S.

Besides, the light-shielding member F is made of light-proof material. Also, the light-shielding member F is formed in such a way that the external diameter of the light-shielding member F approximately corresponds with the internal diameter of the second lens barrel $T_2$, the light-shielding member F is fitted to the second lens barrel $T_2$ in such a way that a gap does not occur, and the light-shielding member F is fixed to the second lens barrel $T_2$ with a light-proof adhesive.

As described above, the optical unit of the present embodiment comprises the optical system by which a front object and an approximately lateral object can be simultaneously observed with the lens $L_{21}$ that is the optical element, so that it is possible to restrain the occurrence of stray light inside the optical system, as compared with prior optical units. That is to say, the light-shielding member F which is made of light-proof material is arranged nearer to the image side than the second lens group $G_2$ which includes the lens $L_{21}$ that is the optical element, so that it is hard for stray light occurring nearer to the object side than light-shielding member F to reach the image plane. As a result, it is possible to effectively reduce flare and ghost.

Figure 8:
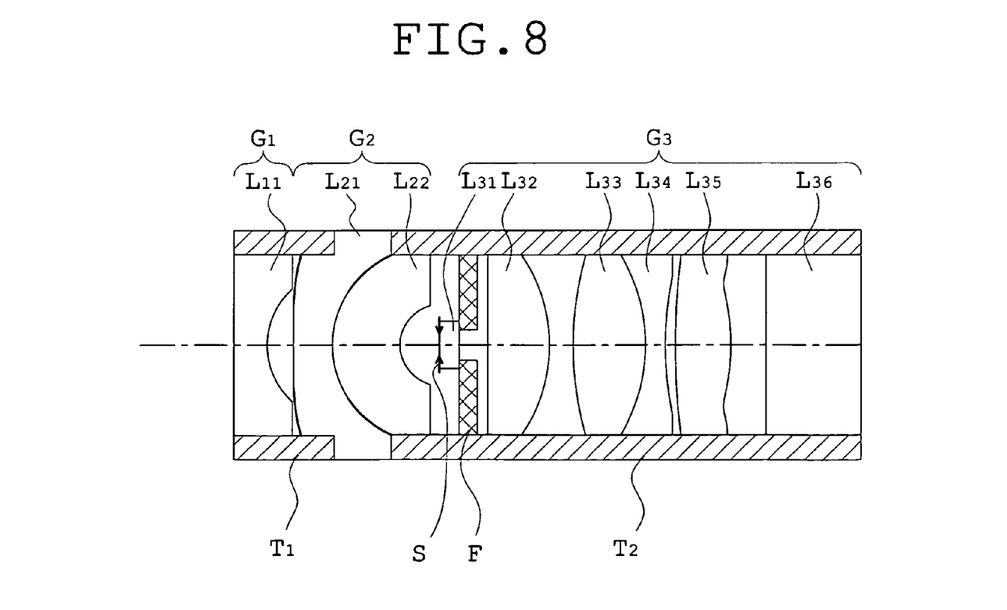
FIG. 8 is a schematic view showing a variation of the optical unit according to the embodiment 2 of the present invention.

Next, a variation of the optical unit according to the embodiment 2 is explained using FIG. 8. In this optical unit which is different from the optical unit of the embodiment 2, the light-shielding member F is arranged between: the lens $L_{31}$ nearest to the object side in the third lens group $G_3$; and the lens $L_{32}$ on the image side of the lens $L_{31}$. Such a constitution also makes it possible for the optical unit of this variation to have the same effects as those in the optical unit of the embodiment 2.

Figure 9:
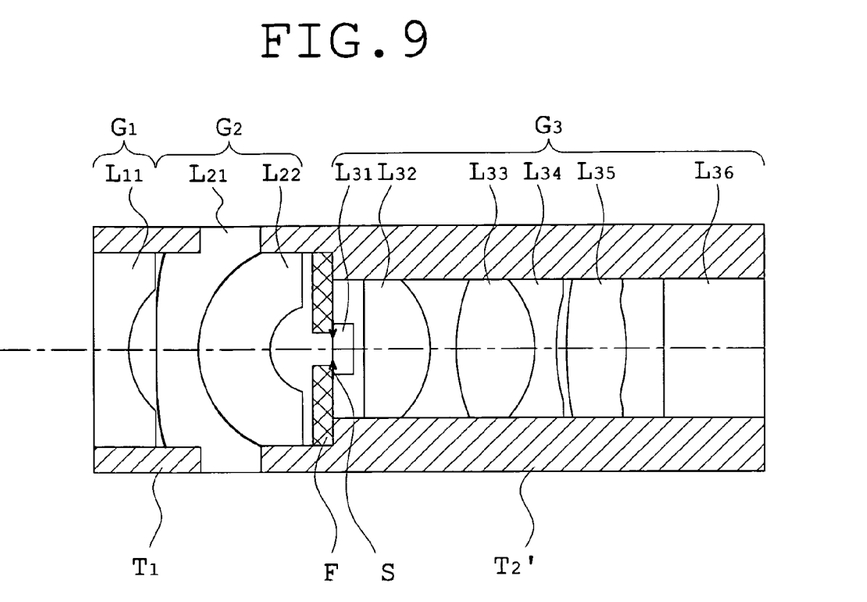
FIG. 9 is a schematic view showing a variation of the optical unit according to the embodiment 2 of the present invention.

Next, another variation of the optical unit according to the embodiment 2 is explained using FIG. 9. In this optical unit which is different from the optical unit of the embodiment 2, the shape on the inside of the second lens barrel $T_2'$ that constitutes the lens barrel is formed in the shape of a step so that the internal diameter of the portion of the second lens barrel $T_2'$ which holds the light-shielding member F is larger than the image-side internal diameter of the second lens barrel $T_2'$.

As described above, the portion which holds the light-shielding member F inside the lens barrel is formed in the shape of a step, so that, in this optical unit, stray light which occurs nearer to the object side than the light-shielding member F does not enter the third lens group $G_3$ and imaging element which are nearer to the image side than the light-shielding member F, through a gap between the light-shielding member F and the lens barrel which occurs due to an assembly error or the like. As a result, it is possible to reduce the occurrence of flare and ghost more effectively. In addition, it becomes easy to assemble the optical unit.

Figure 10:
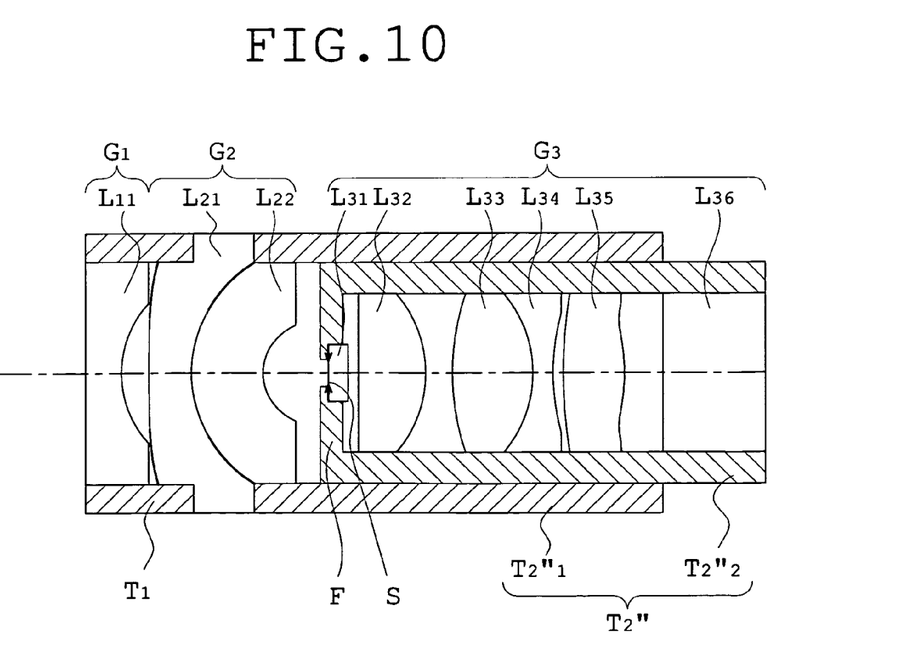
FIG. 10 is a schematic view showing a variation of the optical unit according to the embodiment 2 of the present invention.

Next, another variation of the optical unit according to the embodiment 2 is explained using FIG. 10. In this optical unit which is different from the optical unit of the embodiment 2, the second lens barrel $T_2''$ which constitutes the lens barrel is composed of an external barrel $T_2''_1$, and an internal barrel $T_2''_2$ that is held on the inside of the external barrel $T_2''_1$. Also, the light-shielding member F is integratedly formed in the object-side edge plane of the internal barrel $T_2''_2$. Besides, both of the internal barrel $T_2''_2$ and the light-shielding member F that is formed integratedly with the internal barrel $T_2''_2$ are made of light-proof material.

As described above, the light-shielding member F is formed integratedly with the internal barrel $T_2''_2$ which holds the third lens group $G_3$, so that, in this optical unit, stray light which occurs nearer to the object side than the light-shielding member F does not enter the third lens group $G_3$ and imaging element which are nearer to the image side than the light-shielding member F, through a gap between the light-shielding member F and the internal barrel $T_2''_2$ which occurs due to an assembly error or the like. As a result, it is possible to reduce the occurrence of flare and ghost more effectively. Also, it also becomes easy to assemble the optical unit. In addition, the third lens group $G_3$ can be assembled separately from the other lens groups, so that it also becomes easy to assemble the optical unit and to adjust eccentricity for the optical system.

Besides, in this optical unit, although the second lens barrel $T_2''$ is composed of the external barrel $T_2''_1$ and the internal barrel $T_2''_2$ that is held on the inside of the external barrel $T_2''_1$, the second lens barrel $T_2''$ of this optical unit is not limited to such a constitution, and the second lens barrel $T_2''$ may be composed of three or more members.

Figure 11:
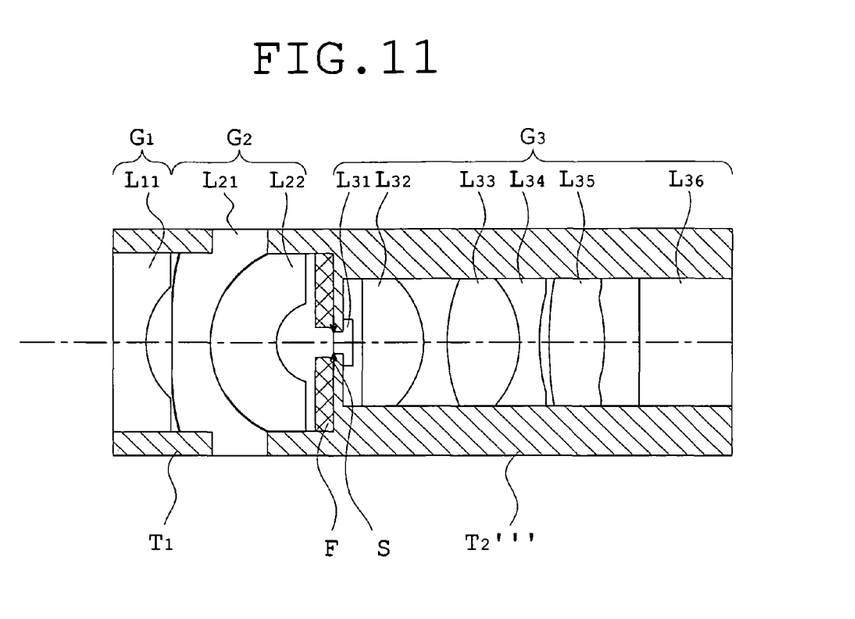
FIG. 11 is a schematic view showing a variation of the optical unit according to the embodiment 2 of the present invention.

Next, another variation of the optical unit according to the embodiment 2 is explained using FIG. 11. In this optical unit which is different from the optical unit of the embodiment 2, the aperture stop S is integratedly formed between a position at which the second lens barrel $T_2'''$ constituting the lens barrel holds the light-shielding member F and a position at which the second lens barrel $T_2'''$ holds the third lens group $G_3$. Also, the second lens barrel $T_2'''$ is formed in such a way that the internal diameter of the second lens barrel $T_2'''$ which is nearer to the object side than the integratedly formed aperture stop S is larger than the image-side internal diameter of the second lens barrel $T_2'''$.

As described above, the aperture stop S is formed integratedly with the second lens barrel $T_2'''$, so that, in this optical unit, stray light which occurs nearer to the object side than the light-shielding member F does not enter the third lens group $G_3$ and imaging element which are nearer to the image side than the light-shielding member F, through a gap between the light-shielding member F and the second lens barrel $T_2'''$ which occurs due to an assembly error or the like. As a result, it is possible to reduce the occurrence of flare and ghost more effectively. Also, it also becomes easy to assemble the optical unit. In addition, the third lens group $G_3$ can be assembled separately from the other lens groups, so that it also becomes easy to assemble the optical unit and to adjust eccentricity for the optical system.

Besides, the present invention is not limited to these examples, and the present invention also includes various combinations of the above-described embodiments and variations.

Also, in the above-described embodiments, the optical systems by which a front object and an approximately lateral object can be simultaneously observed are composed of three lens groups. However, optical systems which are provided for optical units of the present invention are not limited to these examples, and the optical systems may be composed of two lens groups or composed of four or more lens groups.

Also, lenses which constitute lens groups of the optical systems that are provided for optical units of the present invention are not limited to the shapes and the numbers of the lenses which are described in the above-described embodiments, and optical units of the present invention also includes various optical systems including the optical element.

Also, in the above-described embodiments and variations, the light-shielding members are arranged nearest to the object side in the third lens group, or on the image side of the lens nearest to the object side in the third lens group. However, a position of light-shielding member arranged is not limited to the above-described positions. Besides, in order to improve an effect of restraining flare and ghost, it is preferred that the light-shielding members are arranged at a position which is nearer to the object side than the lens nearest to the image side in the third lens group.

Optical units according to the present invention as described above can be used for imaging apparatuses, in particular, such as imaging apparatus for endoscope, in which imaging is performed by forming on an imaging element like CCD the image of an object that is formed by an optical system included by each of the optical units. One specific example of the imaging apparatuses is illustrated below.

Figure 12:
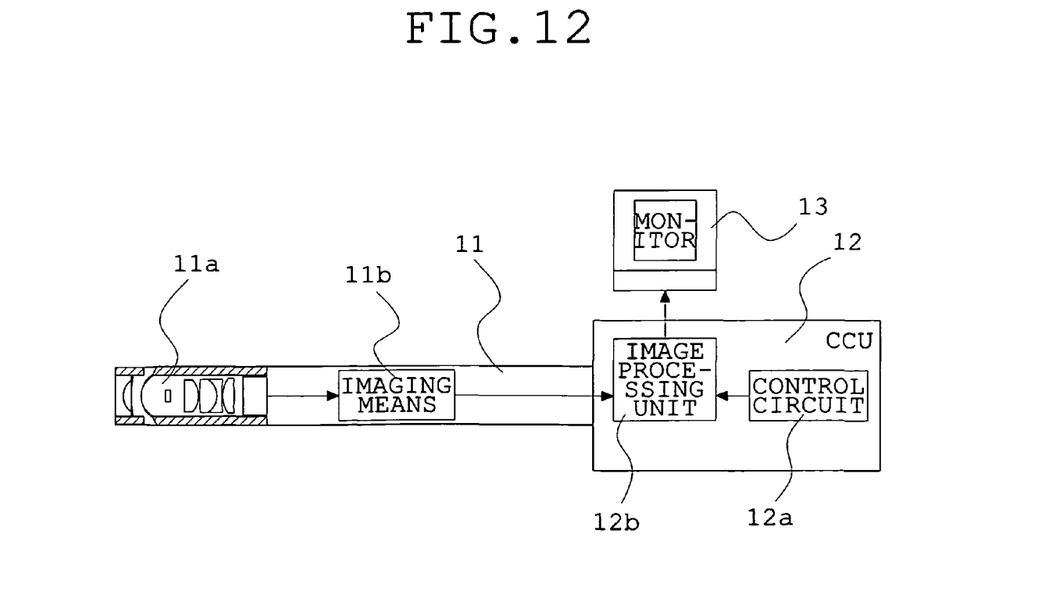
FIG. 12 is a schematic view showing an endoscope apparatus into which an optical unit of the present invention is incorporated.

An endoscope apparatus includes: an elongated insertion unit 11 which is inserted into a body cavity; a light source device (light source unit) which is not shown in the drawings; a camera control unit (CCU) 12 which detects light forming an image in the top end of the insertion unit 11 to image the light and performs image processing; and a monitor 13 which displays an image that is given image processing by the CCU 12, as shown in FIG. 12.

The insertion unit 11 is provided with a light guide (illumination optical system) for guiding light from the light source device to irradiate the light to observation objects such as inside surface of a body cavity, which is not shown in the drawings. In addition, an optical unit 11a according to the present invention and an imaging element 11b which captures an image of an observation object that is formed by an optical system in the optical unit 11a are provided in the top end portion of the insertion unit 11.

The light source device includes: a light source which emits light in a relatively wide wavelength range, for example, like xenon lamp, halogen lamp, white LED, or near-infrared LED; and a filter turret which selectively extracts light of plural kinds of wavelengths from light emitting from the light source.

The CCU 12 includes a control circuit 12a which maps timing of a change of respective filter components of the filter turret onto an image acquired by the imaging element 11b; and an image processing unit 12b which processes the acquired image.

Besides, the imaging element 11b may be provided not in the top end portion of the insertion unit 11 but inside the CCU 12. In this case, an image guide which guides light from the optical system in the range from the image side of the optical unit to the base end-side of the insertion unit 11 should be provided.

INDUSTRIAL APPLICABILITY

An optical element according to the present invention and an optical unit using the same can restrain the deterioration of the capability of forming an image, so that the optical element and the optical unit can be preferably used for endoscopes or the like and are extremely useful for practical use.

The invention claimed is:
1. An optical element, wherein
the optical element is provided with a first surface which is formed on a front-object side and through which light from the front-object side enters, a second surface which is formed on an image side, and a third surface which is formed between the first and second surfaces and through which light from an approximately-lateral-object side enters,
the first surface is provided with a first transmission surface which is formed with a center of the first transmission surface being on an optical axis and a first reflection surface which faces toward the image side and is formed around the first transmission surface and in the shape of a ring, and
the second surface is provided with a second transmission surface which is formed with a center of the second transmission surface being on the optical axis and a second reflection surface which faces toward the front-object side and is formed around the second transmission surface and in the shape of a ring.

2. The optical element according to claim 1, wherein
after the light from the front-object side is incident on the first transmission surface, the light emerges from the second transmission surface to the image side, and
after the light from the approximately-lateral-object side is incident on the third surface, the light is reflected by the second reflection surface and the first reflection surface in that order and emerges from the second transmission surface to the image side.

3. An optical unit, wherein
the optical unit is provided with an optical system by which a front object and an approximately lateral object are observed, and a lens barrel which holds the optical system,
the optical system includes the optical element according to claim 1,
the lens barrel is provided with a first lens barrel and a second lens barrel,
the first lens barrel is fitted to the first surface of the optical element, and
the second lens barrel is fitted to the second surface of the optical element.

4. The optical unit according to claim 3, wherein
an external peripheral surface of the optical unit is composed of an external peripheral surface of the lens barrel and the third surface.

5. The optical unit according to claim 3, wherein
the optical system comprises a first optical system and a second optical system,
the first optical system is provided with a first lens group having negative refractive power, a second lens group including the optical element, and a third lens group in order from the front-object side, and
the second optical system is provided with the second lens group and the third lens group in order from the approximately-lateral-object side.

6. The optical unit according to claim 3, wherein
a first fitting portion is formed around the first reflection surface of the optical element,
a second fitting portion is formed around the second reflection surface of the optical element,
the first lens barrel is fitted to the first fitting portion, and
the second lens barrel is fitted to the second fitting portion.

7. The optical unit according to claim 6, wherein
at least one of the first and second fitting portions is formed in the shape of a step.

8. The optical unit according to claim 7, wherein
the first and second fitting portions are formed to be rotationally symmetric with respect to the optical axis.

9. The optical unit according to claim 3, wherein
the first lens barrel includes a first holding portion,
the second lens barrel includes a second holding portion,
the first holding portion holds the optical element through the first surface of the optical element and the second holding portion holds the optical element through the second surface of the optical element, and
at least one of the first and second holding portions is formed in the shape of a step.

10. The optical unit according to claim 9, wherein
the first and second holding portions are formed to be rotationally symmetric with respect to the optical axis.

11. An optical unit, wherein
the optical unit comprises an optical system by which a front object and an approximately lateral object are observed, a lens barrel which holds the optical system, and an imaging element,
the optical system includes: a lens group including the optical element according to claim 1; and a lens group that is arranged nearer to the image side than the lens group including the optical element and that includes an aperture stop, and
the optical unit is provided with an annular light-shielding member which is placed in the vicinity of the aperture stop, is made of light-shielding material, and has an internal diameter that is larger than an internal diameter of the aperture stop and smaller than an internal diameter of the lens barrel.

12. The optical unit according to claim 11, wherein
the aperture stop is formed integrally with the light-shielding member.

13. The optical unit according to claim 11, wherein
the imaging element is held by the lens barrel.

14. The optical unit according to claim 11, wherein
the lens barrel consists of an internal barrel which holds a lens group that is arranged nearer to the image side than the optical element, and an external barrel which holds the internal barrel, and
the light-shielding member is formed integrally with the internal barrel.

15. The optical unit according to claim 11, wherein
an external diameter of the light-shielding member approximately corresponds with the internal diameter of the lens barrel.

* * * * *